US007616009B2

(12) United States Patent
Jakkula et al.

(10) Patent No.: US 7,616,009 B2
(45) Date of Patent: Nov. 10, 2009

(54) METHOD FOR MICROWAVE MEASUREMENT, MEASURING DEVICE AND OSCILLATOR

(75) Inventors: Pekka Jakkula, Oulu (FI); Taavi Hirvonen, Oulu (FI); Juha Heikkinen, Temmes (FI); Taisto Soikkeli, Kiiminki (FI); Olavi Hyry, Kempele (FI); Jarmo Karhu, Oulu (FI)

(73) Assignee: Senfit Oy, Oulu (FI)

( * ) Notice: Subject to any disclaimer, the term of this patent is extended or adjusted under 35 U.S.C. 154(b) by 205 days.

(21) Appl. No.: 11/662,449

(22) PCT Filed: Sep. 19, 2005

(86) PCT No.: PCT/FI2005/050321

§ 371 (c)(1),
(2), (4) Date: Mar. 9, 2007

(87) PCT Pub. No.: WO2006/032730

PCT Pub. Date: Mar. 30, 2006

(65) Prior Publication Data

US 2007/0268024 A1 Nov. 22, 2007

(30) Foreign Application Priority Data

Sep. 20, 2004 (FI) .................................. 20045348

(51) Int. Cl.
*G01R 27/04* (2006.01)
*G01R 27/32* (2006.01)

(52) U.S. Cl. ....................................... 324/644; 324/642

(58) Field of Classification Search ................. 324/644, 324/642
See application file for complete search history.

(56) References Cited

U.S. PATENT DOCUMENTS

| 3,514,703 | A | 5/1970 | Hiromu |
| 3,737,770 | A | 6/1973 | Masson et al. |
| 5,379,110 | A * | 1/1995 | Matsui et al. ................ 356/445 |
| 6,198,293 | B1 * | 3/2001 | Woskov et al. .............. 324/637 |
| 6,297,648 | B1 | 10/2001 | Lunden |
| 6,297,707 | B1 * | 10/2001 | Martheli et al. ................ 331/96 |
| 6,861,844 | B1 * | 3/2005 | Verdeyen et al. ............. 324/464 |
| 7,263,447 | B2 * | 8/2007 | Strang ......................... 702/49 |

FOREIGN PATENT DOCUMENTS

| GB | 1118096 | 6/1968 |
| GB | 1331525 | 9/1973 |
| JP | 60-042609 | 3/1985 |

* cited by examiner

*Primary Examiner*—Amy He
(74) *Attorney, Agent, or Firm*—Hoffmann & Baron, LLP

(57) ABSTRACT

An object to be measured is measured using microwave radiation. Oscillation energy is generated by means of a feedback coupled active unit. The solution involves generating resonance into at least one oscillator, each oscillator comprising at least one open resonator, each resonator being coupled to at least one active unit, by using the object to be measured as a functional part of the resonator, the object to be measured causing a resonance frequency dependent on the location of a surface of the object to be measured to be generated in each oscillator. A measurement part determines at least one characteristic of the object to be measured on the basis of the resonance frequency of each oscillator.

19 Claims, 4 Drawing Sheets

METHOD FOR MICROWAVE MEASUREMENT, MEASURING DEVICE AND OSCILLATOR

CROSS-REFERENCE TO RELATED APPLICATION

This application is a National Phase application of International Application No. PCT/FI2005/050321 filed Sep. 19, 2005, which claims priority based on Finnish Patent Application No. 20045348, filed Sep. 20, 2004, which are incorporated herein by reference.

BACKGROUND OF THE INVENTION

1. Field of the Invention

The invention relates to a method for microwave measurement of an object to be measured, at least the surface of which is made of an electrically conductive material. The invention also relates to a measuring device and an oscillator.

2. Description of the Related Art

In an electrically conductive, usually flat piece the thickness of the piece and/or also some other dimension parallel with its thickness may be measured using microwave measurement in which the resonance frequency of the measurement resonator depends on a thickness dimension of the piece to be measured. For example, a cylindrical resonator or a Fabry-Perot resonator may be used for this purpose. The resonator frequency can be found by scanning the frequency of an oscillator producing microwave radiation over a measurement band. The thickness dimension of the piece to be measured can then be determined as a function of the found resonator frequency.

However, frequency scanning involves a number of problems. A measuring device based on frequency scanning is complicated and expensive, because it requires scanning electronics that change the oscillator frequency. In addition, frequency scanning is time-consuming, because the measurement must be carried out at all measurement band frequencies and thus it takes time before the measurement results are obtained. Measuring the thickness of a moving and shaking plate by means of a frequency scanning application is problematic, because it is not possible to carry out a rapid, synchronic and perfectly simultaneous measurement of distance on both sides of the plate.

SUMMARY OF THE INVENTION

It is an object of the invention to provide an improved method for microwave measurement, a measuring device and an oscillator. This is achieved by a method for measuring an object to be measured by means of microwave radiation, comprising producing oscillation energy for an oscillator by means of an active feedback coupled unit. The method comprises generating resonance to at least one oscillator, each oscillator comprising at least one open resonator, each resonator being coupled to at least one active unit, by using the object to be measured as a functional part of the resonator, whereby the object to be measured causes a resonance frequency dependent on the location of a surface of the object to be measured to be generated in each oscillator; and determining at least one characteristic of the object to be measured on the basis of the oscillator resonance frequency by using a measurement part.

The invention also relates to a measuring device for measurement at a microwave frequency, the measuring device comprising at least one oscillator operating at a microwave frequency, each oscillator comprising a feedback coupled active unit for generating oscillation energy. The oscillator comprises at least one open resonator, each resonator being coupled to at least one active unit; each active unit supplies oscillation energy to each resonator at the moment of measurement, the object to be measured being meant as a functional part of the resonator and the object to be measured being configured to cause resonance in the oscillator; each open resonator is configured to determine the resonance frequency of each oscillator on the basis of the location of a surface of the object to be measured; and the measuring device comprises a measurement part configured to determine at least one characteristic of the object to be measured on the basis of the resonance frequency of each oscillator.

The invention further relates to an oscillator for measurement at a microwave frequency, the oscillator comprising a feedback coupled active unit for generating oscillation energy. The oscillator comprises at least one open resonator coupled to the active unit; the active unit supplies oscillation energy to the resonator, the object to be measured being meant as a functional part of the resonator and the object to be measured being configured to cause resonance in the oscillator; and the open resonator is configured to determine the resonance frequency of an oscillator on the basis of the location of a surface of the object to be measured.

Preferred embodiments of the invention are disclosed in the dependent claims.

The method and arrangement of the invention provide a number of advantages. Resonator frequency can be determined without frequency scanning, which renders the solution fast, simple and cost-effective in this respect. In addition, the measurement can be used for measuring a characteristic of a shaking plate.

BRIEF DESCRIPTION OF THE DRAWINGS

The invention will be described in greater detail with reference to preferred embodiments and the accompanying drawings, in which.

DETAILED DESCRIPTION OF THE PREFERRED EMBODIMENTS

The disclosed solution is applicable to the measurement of objects having an electrically conductive surface. Its applications include, although are not restricted to, objects made of metal, such as plates of steel, copper or aluminium, or insulating plates coated with an electrically conductive substance.

Figure 1:
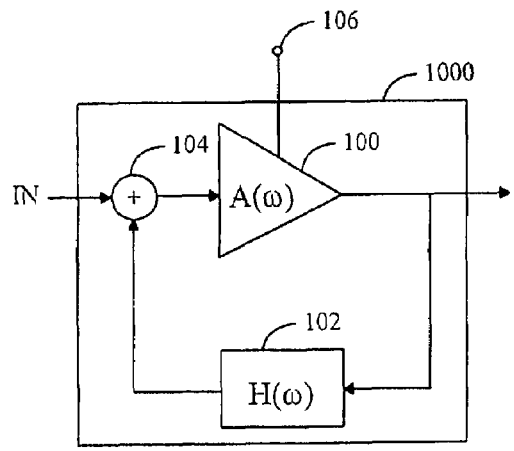
FIG. 1 illustrates an oscillator based on a feedback coupled amplifier.

With reference to FIG. 1, let us examine first a feedback coupled oscillator. An oscillator 1000 comprises an active unit 100, a feedback coupling element 102 and a summer 104. The active unit 100 may contain one or more active electronic components. An active component is a component that requires operating voltage and current supplied from an electrical power source (not shown in FIG. 1) to a terminal 106 in order to operate. Transistors, for example, are active components. The feedback coupling element 102 may contain one or more passive components that do not need operating voltage or current to operate. The summer 104 is not necessarily needed at all, because a signal from the feedback coupling element 102 is sufficient as an input signal for the oscillator, or the summer 104 may be implemented simply with wires coupled to each other.

Oscillator feedback coupling is usually implemented using positive feedback coupling. The transfer function T(ω) of the coupling of FIG. 1 takes the following format:

$$T(\omega)=A(\omega)/[1-H(\omega)A(\omega)], \qquad (1)$$

where ω2πf, f is frequency, π≈3.1415926, A(ω) is the amplification/transfer function of the active component as a function of frequency, H(ω) is the transfer function of the feedback coupling element as a function of frequency. The coupling of FIG. 1 may produce an oscillator, provided that it fulfills two conditions of the Barkhausen criterion: the phase shift of an open loop must be 2πn, n=0, 1, 2, . . . (positive feedback coupling) and the open loop amplification H(ω)A(ω) must be >1 in the entire measurement band desired. The active unit 100 is thus taken to an unstable state by means of feedback coupling, and by means of a suitable resonator the coupling can be made to resonate at the resonator frequency.

Figure 2:
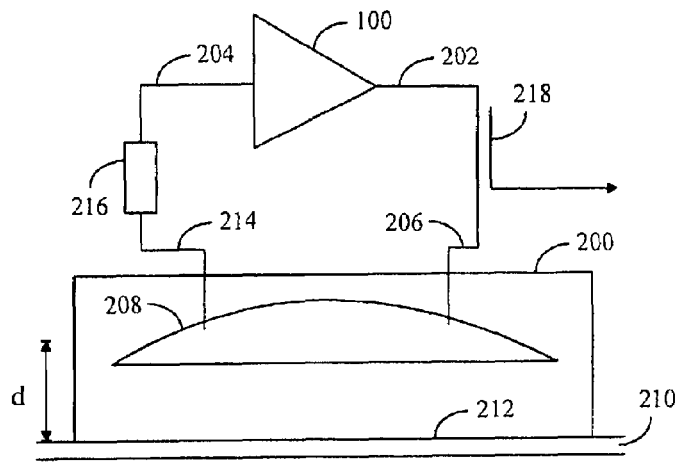
FIG. 2 illustrates an oscillator with an open resonator and a two-port coupling.

FIG. 2 shows an oscillator solution suitable for microwave measurement. This two-port solution employs two parallel feedback couplings, an open resonator 200 being coupled between an output 202 and an input 204 of the active unit 100. From the active unit 100 microwave radiation is supplied to the resonator 200 on a transfer line 206, the radiation being directed to the object to be measured 210 by means of a mirror 208 of the resonator. The microwave radiation is reflected back from the object to be measured 210, whereby the resonator 200 is provided with a resonant stationary wave dependent on a distance d between the upper surface 212 of the object to be measured 210 and the resonator mirror 208. The length of the stationary wave is a multiple of a half of the wavelength, mathematically expressed as $$d = n \cdot \frac{\lambda}{2},$$

where n is an integer 1, 2, . . . and λ is the wavelength. The shape of the mirror may be a curved spherical surface, although a paraboloid or some other surface shape directing microwave radiation to the object to be measured is also possible.

Thus when the distance between the resonator mirror 208 and the upper surface 212 of the object to be measured 210 changes due to changes in the thickness of the object to be measured 210, for example, also the wavelength λ of the resonant microwave radiation changes without outside measures. A generalized statement would be that the wavelength of a resonant microwave radiation changes when a characteristic of the object to be measured or affecting the object changes. For example, the object to be measured may be subjected to a force pulling the object further away from (or closer to) the resonator mirror. If the distance between the object to be measured and the resonator mirror changes, a physical characteristic of the object or a characteristic affecting the object, such as force, can be determined. In this solution resonance frequency does not need to be searched for by means of scanning or any other way either, but the resonator 200 directly determines the oscillation frequency/frequencies of the oscillator. The open resonator 200 may thus be a Fabry-Perot type resonator. The resonant microwave radiation is received for example on a transfer line 214 and after a phase shift possibly carried out in a phase shifter 216 the received microwave radiation is coupled back to the active unit 100 that generates oscillation energy to maintain resonance in the oscillator. Part of the resonant frequency signal from the output 202 of the active unit 100 can be further transferred to measurement, for example, by means of a directional coupler 218, for example.

Figure 3:
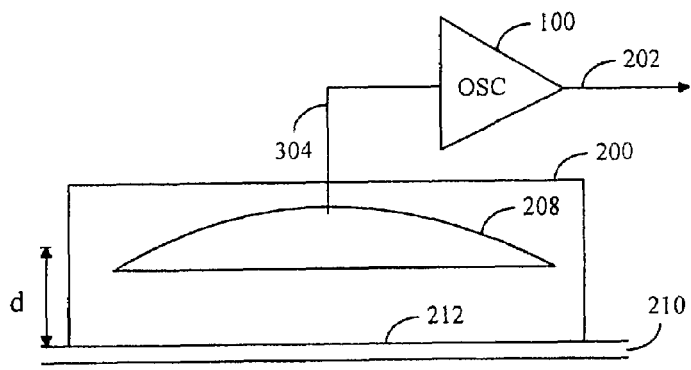
FIG. 3 illustrates an oscillator with an open resonator and a single-port coupling.

FIG. 3 illustrates a serial feedback coupling, in which the open resonator 200 is coupled to an input 304 of the active unit 100. The feedback coupling may be incorporated into the active unit 100, in which case the active unit functions as an oscillator. This solution may also be called a single-port coupling. Via the transfer line 304 the microwave radiation passes to the open resonator 200 whose mirror 208 directs the radiation to the object to be measured 210. The microwave radiation is reflected back by the object to be measured 210, whereby a resonant stationary wave dependent on the distance d between the resonator mirror 208 and the upper surface 212 of the object to be measured 210 is formed. Thus when the distance between the resonator mirror 208 and the upper surface 212 of the object to be measured 210 changes due to changes in the thickness of the object to be measured 210, for example, also the wavelength λ of the resonant microwave radiation changes, similarly as in FIG. 1. The resonant microwave radiation is received on the same transfer line 304 that was used for supplying it to the resonator 200. The received microwave radiation passes to the active unit 100 that generates oscillation energy to maintain resonance in the oscillator thus formed. From the output 202 of the active unit 100 the resonant frequency signal can be conveyed further to measurement, for example.

As shown in FIGS. 2 and 3, the oscillator comprises the open resonator 200 coupled to the active unit 100. The open resonator 200 directs microwave radiation to a direction in which the object to be measured 210 and reflecting microwave radiation is meant to act as a functional part of the resonator at the moment of the measurement. The open resonator 200 thus determines the resonance frequency of the oscillator according to the location of the surface 212 of the object to be measured 210. In general an oscillator may also comprise more than one open resonator. It is also possible to have a plural number of oscillators.

Figure 4:
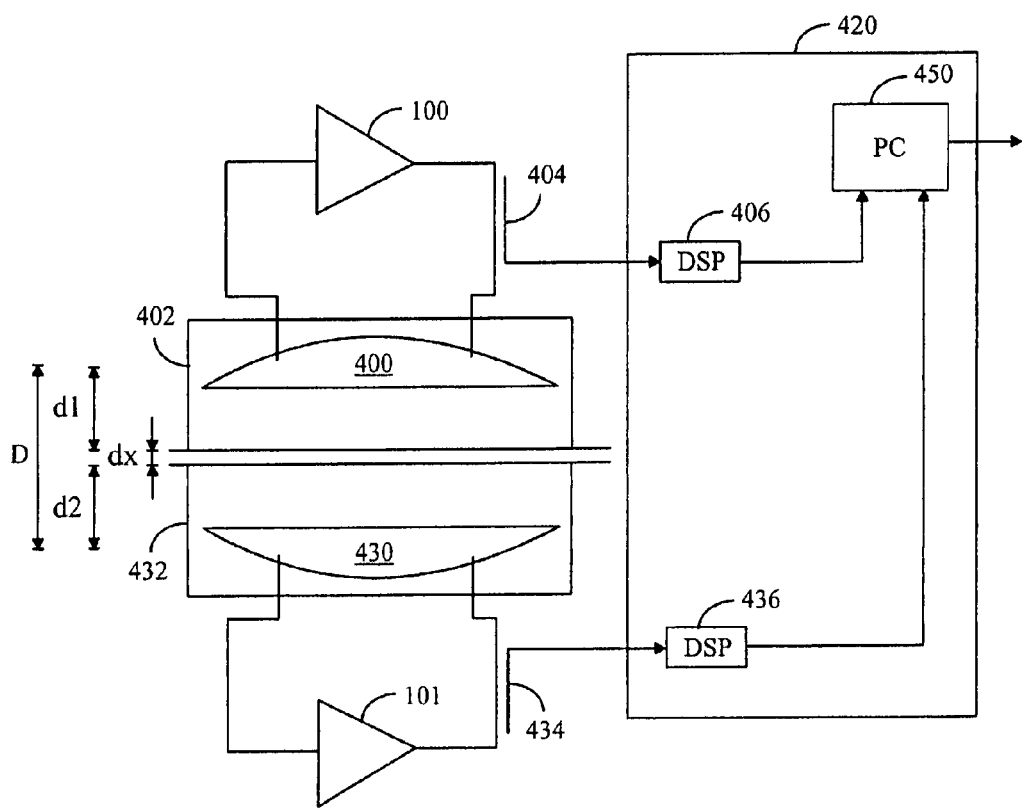
FIG. 4 illustrates measurement by means of a resonator pair.

FIG. 4 is a block diagram of a measuring device whose operation is based on microwaves. The aim is to use the measuring device to measure at least one characteristic of the object to be measured. This solution employs two open resonators directed to face each other and meant to have the object to be measured between them at the moment of measurement. Two resonators facing each other form a resonator pair. When the object to be measured 210 is brought between resonator mirrors 400, 430 facing each other, two resonators 402, 432 are produced. The resonance frequency of the resonator 402 is determined by the distance between the resonator mirror 400 and the upper surface 212 of the object to be measured 210. Correspondingly, the resonance frequency of the resonator 432 is determined by the distance between the resonator mirror 430 and the lower surface 213 of the object to be measured 210. The active unit 100, which is tuned to a non-stable state, generates energy for the resonator 402 and produces with the resonator 402 an oscillator resonating at the resonance frequency of the resonator 402. Correspondingly, the active unit 101, which is tuned to a non-stable state, generates energy for the resonator 432 and produces with the resonator 432 an oscillator resonating at the resonance frequency of the resonator 432. The output signal of the active unit 100 may be coupled to a measurement part 420 comprising a digital signal processing unit 406, for example, by means of a directional coupler 404. The signal processing unit 406 may determine a distance d1 on the basis of the resonance frequency. This may be carried out by calculating d1 from the following formula of resonance frequency f:

$$f = c(q+1+((2p+l+1)/p))\arctan((d1/(r_0-d1))^{1/2})) \quad (2)$$

where f is the resonance frequency of microwave radiation, c is the speed of microwave radiation, $r_0$ is the radius of the spherical surface of the mirror, and p, l and q are indices of the resonance form, q+1 being the number of half-waves in the resonator.

The output signal of the active unit 101 may be connected to the measurement part 420 comprising a digital signal processing unit 436, for example, by means of a directional coupler 434. The signal processing unit 436 determines a distance d2 on the basis of the resonance frequency. This may be carried out similarly as for the distance d1. The measurement data of the signal units 406, 436 may be entered into a computer 450 that may form a thickness dimension of the object to be measured 210.

In practice, separate signal processing units 406, 436 are usually not needed in the measurement part 420, but signal processing may take place in a common signal processing unit. In fact separate signal processing units 406, 436 and a separate computer 450 are often not necessarily used, but signals coming from the directional couplers 404, 434 may be processed for example in a digital signal processing device functioning as the measurement part 420 and producing the necessary measuring results.

Assuming that a distance D between the resonator mirrors 400, 430, which is usually kept as an invariable to the extent possible, is known at the moment of measurement, a thickness dx of the object to measured can be determined in the computer 450 for example by applying the following equation:

$$dx = D - (d1 + d2), \quad (3)$$

where d1 is the distance of the mirror 400 from the upper surface 212 of the object to be measured 210 and d2 is the distance of the mirror 430 from the lower surface 213 of the object to be measured 210. If the distance D between the resonator mirrors changes due to thermal expansion, for example, resonance frequency f may be calculated from the resonator formed by two mirrors facing each other by applying the following formula:

$$f = c(q+1+((2p+l+1)p)\arccos(1-D/Ro))/2D \quad (4)$$

Automated calibration of a measuring device based on the above will be described further below.

Figure 5:
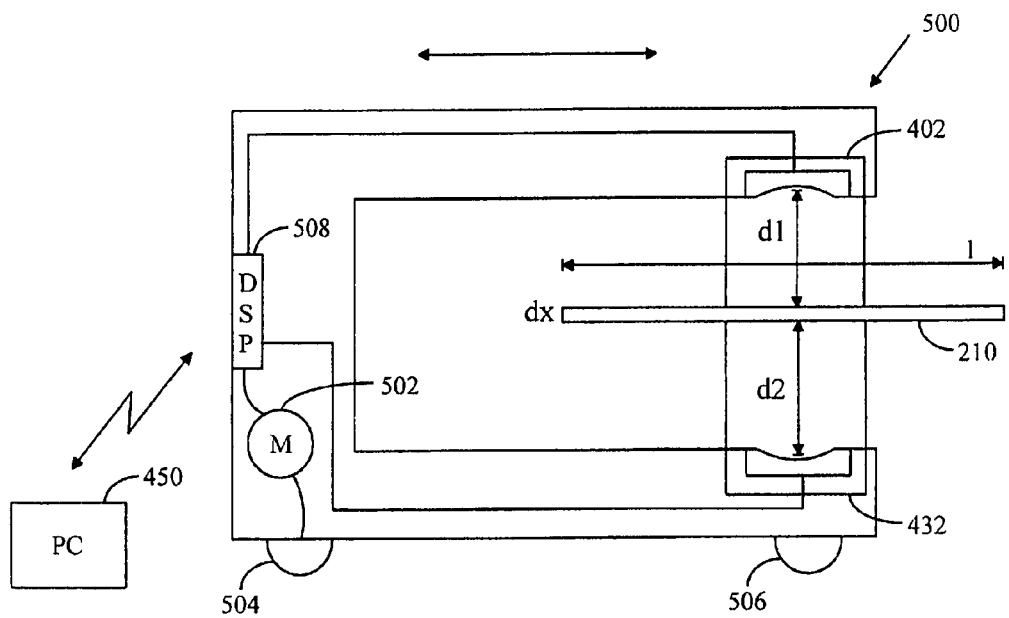
FIG. 5 illustrates a scanning measurement frame.

FIG. 5 illustrates a solution in which the resonator pair can be mechanically moved on both sides of the object to be measured 210. A measurement frame 500 may comprise wheels 504, 506 on which the measurement frame rests against the floor, for example, and which allow the measurement frame 500 to be moved. In a controlled transfer there may be a motor 502 to turn the wheels 504 taking the resonators 402, 432 to the desired starting points for measurement. The computer 450 then controls the motor 502 to take the resonators 402, 432 across the surface of the object to be measured, i.e. to scan the object to be measured 210, a digital signal processing device 508 measuring the distances d1 and d2 at a plural number of measurement points. From the measurement data the digital signal processing device 406 may establish for example the thickness dx of the object to be measured as a function of width l: dx(i)=D−[d1(i)+d2(i)], where i is the measurement point index in the direction of width.

Figure 6:
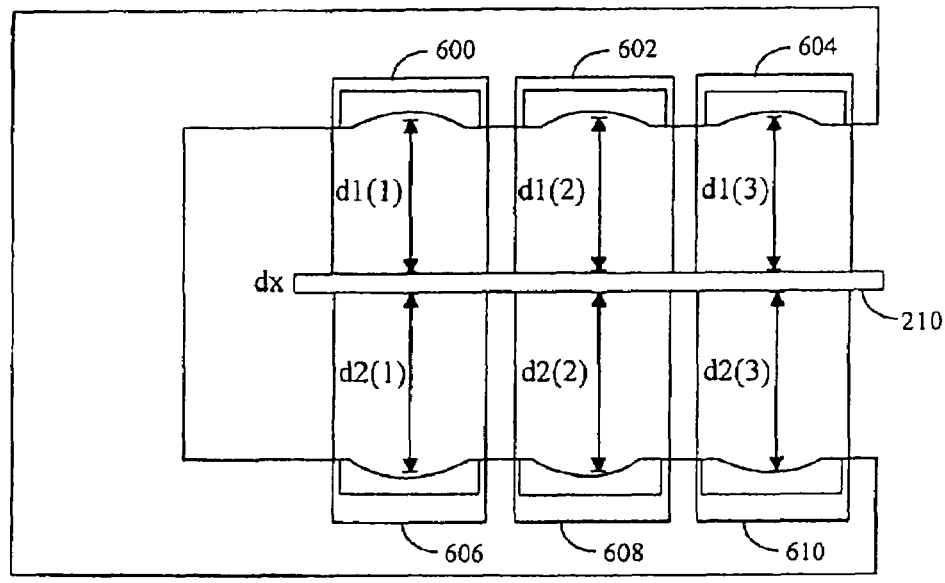
FIG. 6 illustrates a measurement frame comprising a plural number of resonator pairs.

FIG. 6 illustrates a solution in which the measurement frame comprises a plural number of parallel resonators on both sides of the object to be measured 210. Resonators placed on different sides of the object to be measured may be arranged in pairs facing each other as in FIG. 6. Measurements of the object to be measured 210 may be taken according to the locations of the resonators 600-610. Thus for example the following thickness values may be determined: dx(i)=D−[d1(i)+d2(i)], i.e. dx(1)=D−[d1(1)+d2(1)], dx(2)=D−[d1(2)+d2(2)] and dx(3)=D−[d1(3)+d2(3)]. Although this solution can be used instead of scanning the surface of the object to be measured with resonators, it can also be used with scanning.

Instead of or in addition to thickness, also the profile of the object may be measured. In this case the object to be measured is measured at several points in accordance with a predetermined straight line, similarly as in thickness measurement. Each profile is measured by taking into account the dimensions d1 and d2, whereby the variation in thickness and shape of the surface on the line of measurement is obtained.

An object can also be measured with regard to its flatness, which may be determined as longitudinal variation in the back line of the object to be measured.

Figure 7:
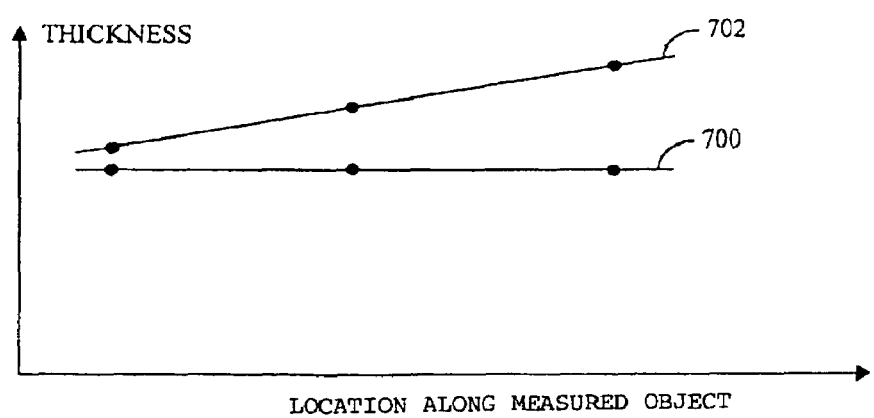
FIG. 7 illustrates a deflection of a measurement frame.

A measuring device comprising parallel resonators, such as the one in FIG. 6, can also be used for measuring a deflection of the measurement frame and it can then be cancelled by compensation from the measurement of the object to be measured. For example, measurement of an object by means of a measuring device of FIG. 6 may produce a thickness curve 700 like the one shown in FIG. 7, when the measuring device is used immediately after it has been manufactured to measure a straight reference plate of a uniform thickness, whereas after a long-term use (e.g. a year) the result produced by the measuring device may be as shown by curve 702. The change in the angular coefficient of the straight line is due to the deflection in the measurement frame shown by the curves 700 and 702 to form a small angle, i.e. shortening has affected most the distance between the resonators 604 and 610. Since the object to be measured has not changed, the measurement results relating to the object of measurement may be amended in a computer or a signal processing device.

When two resonators facing each other are used, as in FIGS. 4 to 6, the measuring device may calibrate itself automatically in the following manner. When there is no actual object of measurement between the resonators, the measuring device may use the resonator mirrors as the object to be measured. In this case the measuring device measures the distance D between the resonator mirrors, which distance should not change, i.e. it has been determined in advance. The measurement result may change if there is dirt on the mirrors, the shape of the mirrors has changed, or air humidity or density inside the resonator has changed. The effect of all of these can be compensated for in the actual measurements of the object of measurement, thus improving the accuracy of measurement. There is no object to be measured between the resonators if, for example, production has been cut off or interrupted, the measurement frame has been pulled away from the measurement track, or a roller is being provided with a new band when manufacturing a metal sheet. In this calibration measurement measurements taken in opposite directions are based on crosswise polarisations in order to prevent confusion.

Figure 8:
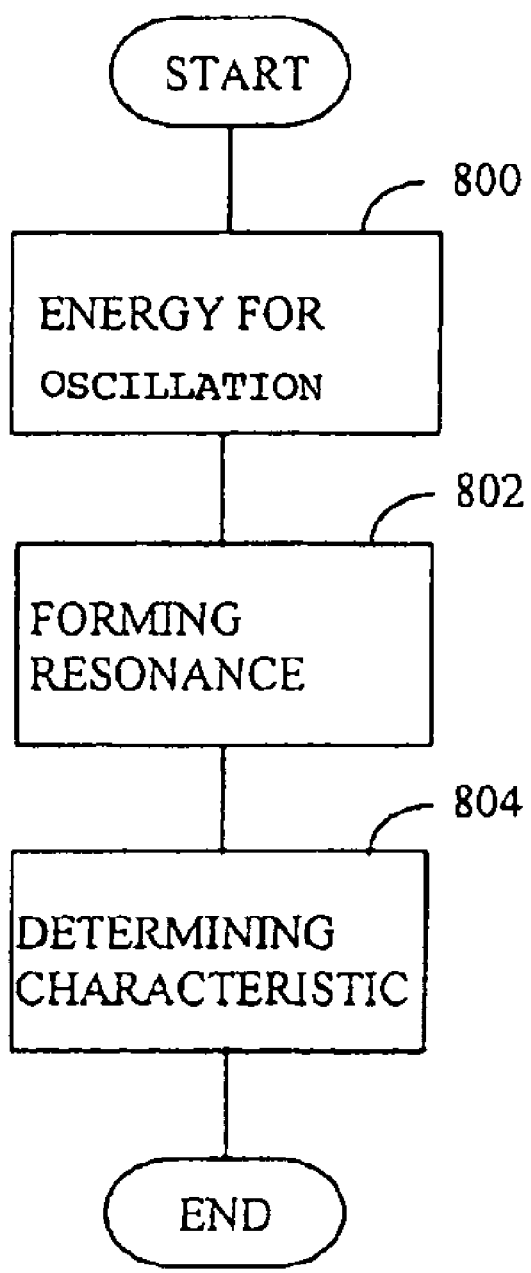
FIG. 8 is a flow diagram of the method.

Next, the disclosed solution will be further examined with reference to the flow diagram of FIG. 8. In step 800 the oscillator is provided with oscillation energy generated by means of a feedback coupled active unit. In step 802 resonance is created in at least one oscillator, each oscillator comprising at least one open resonator 200, each resonator being coupled to at least one active unit 100, by using the object to be measured 210 as a functional part of the resonator, whereby the object to be measured 210 causes in each oscillator resonance frequency dependent on the location of the surface 212 of the object to be measured 210. In step 804 the measurement part 420 is used to determine at least one characteristic of the object to measured 210 on the basis of the resonance frequency of each oscillator. Step 804 may be carried out for example by means of a computer program containing routines for executing the method steps. For sales purposes, for example, the computer program may be stored on a computer readable memory, such as a CD-ROM (Compact Disc Read Only Memory). The computer program may also be included into a telecommunications signal downloadable from a server (across the Internet, for example) into a measuring device.

Instead of a computer program the measuring part 420 may be implemented using a hardware solution for example in the form one or more ASIC circuits (Application-Specific Integrated Circuit) or an operational logic consisting of dedicated components.

Although the invention is disclosed above with reference to the examples of the accompanying drawings, it is obvious that the invention is not restricted thereto but may be varied in many ways within the scope of the accompanying claims.

What is claimed is:

1. A method for measuring an object to be measured by means of microwave radiation, comprising producing oscillation energy for an oscillator by means of an active feedback coupled unit, said method further comprising:
   generating resonance to at least one oscillator, each oscillator comprising at least one open resonator with a mirror, each resonator being coupled to at least one active unit, by using the object to be measured to reflect the microwave radiation directed from the mirror to the object back to the mirror of the resonator, whereby the object to be measured causes a resonance frequency between the mirror and the object dependent on the location of a surface of the object to be measured; and
   determining at least one characteristic of the object to be measured on the basis of the oscillator resonance frequency by using a measurement part without requiring sweeping or scanning microwave radiation.

2. A method according to claim 1, wherein generating resonance comprises using at least one resonator pair directed to face each other and meant to have the object to be measured between them at the moment of measurement.

3. A method according to claim 2, wherein resonance frequencies are generated for the oscillators on the basis of the distances between the object to be measured and the resonators and the determining step determines the thickness of the object to be measured on the basis of the resonance frequencies in the measurement part.

4. A method according to claim 2, wherein generating resonance comprises using a plural number of resonator pairs measuring the object to be measured at a plural number of points, oscillator resonance frequencies are generated on the basis of the distances between the object to be measured and the resonators, and the profile of the object to be measured is determined on the basis of the resonance frequencies in the measurement part.

5. A method according to claim 2, wherein measurements are performed on different sides of the object at the same time.

6. A method according to claim 1, wherein generating resonance comprises using a plural number of resonator pairs measuring the object to be measured at a plural number of points, oscillator resonance frequencies are generated on the basis of the distances between the object to be measured and the resonators, and the flatness of the object to be measured is determined on the basis of the resonance frequencies in the measurement part.

7. A method according to claim 6, wherein for the deflection of a measurement frame is compensated in the measurement part from the measurements of the object to be measured.

8. A method according to claim 1, wherein generating resonance comprises using a plural number of resonator pairs, a predetermined reference point is measured and the deflection of a measurement frame is determined in the measurement part as a difference between a measured characteristic and a predetermined one.

9. A method according to claim 1, wherein generating resonance comprises using a plural number of resonator pairs, whose mirrors are at a predetermined distance from one another, each resonator is arranged to apply the opposite resonator mirror as the object to be measured, the distance between the mirrors of the resonator pairs is determined in the measurement part, and the measurement results are amended according to the difference between the measured distance and the predetermined distance.

10. A measuring device for measurement at a microwave frequency,
    the measuring device comprising at least one oscillator operating at a microwave frequency, each oscillator comprising a feedback coupled active unit for generating oscillation energy, wherein
    the oscillator comprises at least one open resonator with a mirror, each resonator being coupled to at least one active unit;
    each active unit supplies oscillation energy to each resonator at the moment of measurement, the object to be measured being configured to reflect the microwave radiation directed from the mirror to the object back to the mirror of the resonator, the object to be measured causing resonance in the oscillator;
    each open resonator is configured to determine the resonance frequency formed between the mirror and the object on the basis of the location of a surface of the object to be measured; and
    the measuring device comprises a measurement part configured to determine at least one characteristic of the object to be measured on the basis of the resonance frequency of each oscillator without requiring sweeping or scanning microwave radiation.

11. A measuring device according to claim 10, wherein the measuring device comprises at least one resonator pair directed to face each other and to have the object to be measured between them at the moment of measurement.

12. A measuring device according to claim 11, wherein each open resonator is configured to simultaneously determine resonance frequencies according the distances between the object to be measured and each resonator, and the measurement part is configured to determine the thickness of the object to be measured on the basis of the resonance frequencies.

13. A measuring device according to claim 11, wherein when the measuring device comprises at least one resonator pair measuring the object to be measured at a plural number of points, each open resonator is configured to determine resonance frequencies according to the distances between the object to be measured and each resonator, and the measurement part is configured to determine the profile of the object to be measured on the basis of the resonance frequencies.

14. A measuring device according to claim 11, wherein the at least one resonator pair is configured to perform measurements on different sides of the object at the same time.

15. A measuring device according to claim 10, wherein when the measuring device comprises a plural number of resonator pairs measuring the object to be measured at a plural number of points, each open resonator is configured to determine resonance frequencies according to the distances between the object to be measured and each resonator, and the measurement part is configured to determine the flatness of the object to be measured on the basis of the resonance frequencies.

16. A measuring device according to claim 15, wherein the measurement part is configured to compensate for the deflection of a measurement frame from the measurements of the object to be measured.

17. A measuring device according to claim 10, wherein when the measuring device comprises a plural number of resonator pairs, the measuring device is configured to measure a predetermined reference point, the measurement part being configured to determine the deflection of a measurement frame as a difference between a measured characteristic and a predetermined one.

18. A measuring device according to claim 10, wherein when the measuring device comprises a plural number of resonator pairs whose mirrors are at a predetermined distance from one another, the measuring device is configured to use the opposite resonator mirror as the object to be measured for each resonator for calibration purposes, and the measurement part is configured to determine a predetermined distance between the mirrors of the resonator pairs.

19. An oscillator for measurement carried out at a microwave frequency, the oscillator comprising:
  a feedback coupled active unit for generating oscillation energy, wherein
  the oscillator comprises at least one open resonator with a mirror coupled to the active unit;
  the active unit supplies oscillation energy to the resonator, an object to be measured being configured to reflect the microwave radiation directed from the mirror to the object back to the mirror of the resonator, the object to be measured causing resonance in the oscillator; and
  the open resonator is configured to determine the resonance frequency between the mirror and the object on the basis of the location of a surface of the object to be measured without requiring sweeping or scanning microwave radiation.

* * * * *